United States Patent [19]

Walker et al.

[11] 4,167,532

[45] Sep. 11, 1979

[54] DEHYDROGENATION OF ORGANIC COMPOUNDS

[75] Inventors: Darrel W. Walker; Robert J. Hogan; Floyd Farha, Jr., all of Bartlesville, Okla.

[73] Assignee: Phillips Petroleum Co., Bartlesville, Okla.

[21] Appl. No.: 617,754

[22] Filed: Sep. 29, 1975

[51] Int. Cl.$^2$ ............................................. C07C 11/12
[52] U.S. Cl. ...................................... 585/622; 585/658
[58] Field of Search ........................ 260/680 E, 683.3

[56] References Cited

U.S. PATENT DOCUMENTS

| | | | |
|---|---|---|---|
| 3,403,192 | 9/1968 | Vadekar et al. | 260/669 R |
| 3,781,223 | 12/1973 | Walker et al. | 252/437 |
| 3,790,501 | 2/1974 | Walker | 252/437 |
| 3,810,953 | 5/1974 | Cichowski | 260/683.3 |
| 3,845,156 | 10/1974 | Farha | 260/680 E |
| 3,862,997 | 1/1975 | Walker | 260/680 E |
| 3,943,068 | 3/1976 | Ripley | 260/680 E |

*Primary Examiner*—Delbert E. Gantz
*Assistant Examiner*—Joseph A. Boska

[57] ABSTRACT

Hydrocarbon feedstocks are dehydrogenated to compounds having the same number of carbon atoms and a higher degree of unsaturation by contacting the feedstock in the vapor phase in the presence of molecular oxygen with a catalyst consisting essentially of nickel, lead, phosphorus and combined oxygen, and optionally, an alkali metal. Representative of such conversions is the oxidative dehydrogenation of butane to butenes and butadiene.

3 Claims, No Drawings

DEHYDROGENATION OF ORGANIC COMPOUNDS

This invention relates to chemical compositions and to chemical processes. In one aspect this invention relates to catalytic materials. In another aspect this invention relates to catalytic processes for effecting the dehydrogenation of hydrocarbons.

Thermal non-catalytic and catalytic processes for converting organic compounds to compounds having a higher degree of unsaturation are known. The former are characterized by undesirable side reactions, low order of conversion and yields and poor selectivity to desired product. The catalytic processes are characterized by the particular catalytic material employed and the conditions unde which the processes are operated, e.g., in the absence or presence of oxygen. While a number of such catalytic processes have attained some measure of commercial success, there is continuing search for better catalytic materials which exhibit the high activity, high yield to desired product, high selectivity to desired product, extended longevity, which can be readily regenerated to an activity approaching that of fresh catalyst, and which keep undesirable side reactions to a minimum; all characteristics of good dehydrogenation catalysts. The vexatious problem constantly faced by those skilled in the art is the identification and characterization of the compositions which are highly efficient dehydrogenation catalysts.

Among the more recently disclosed dehydrogenation catalysts are those which include halogens or halogen-releasing materials. Such catalysts have exhibited so many disadvantages in regard to equipment corrosion and the additional expense of continuously feeding, recovering and recycling the relatively expensive halogen materials that economically practical, large-scale use of such catalytic materials has been precluded. Halogen-free catalytic materials continue to be the most desirable for use in oxidative dehydrogenation processes.

It is an object of this invention to provide a catalyst composition which has a highly effective catalytic activity. It is another object of this invention to provide a process for the catalytic dehydrogenation of hydrocarbon materials. Other objects and advantages of this invention will become apparent to those skilled in the art from the detailed description of this invention which follows and the appended claims.

In accordance with the present invention, there is provided a novel catalyst and a novel process for the conversion of hydrocarbon feedstocks to hydrocarbons having a greater degree of unsaturation and which have the same or lower number of carbon atoms as the hydrocarbon feed. According to this invention, hydrocarbon feedstocks can be converted directly to hydrocarbons having a greater degree of unsaturation by contacting such feedstocks under dehydrogenation conditions in the vapor phase in the presence of molecular oxygen with a catalytic material consisting essentially of nickel, lead, phosphorus and combined oxygen, and optionally, an alkali metal. Thus, paraffinic hydrocarbons can be converted in good yields to diolefins and/or monoolefins, and monoolefins can be converted to diolefins. This invention is particularly applicable for the production of diolefins from paraffins, and particularly useful results are obtained by the dehydrogenation of butane to butenes and butadiene, and butenes to butadiene.

The hydrocarbon feedstocks which are applicable for the oxidative dehydrogenation processes of the present invention comprise dehydrogenatable aliphatic hydrocarbons having from 2 to about 12 carbon atoms per molecule and at least one

grouping. These can be branched or unbranched and include paraffins as well as monoolefins, but the application of the process for paraffins is presently considered most advantageous. The conversions of butane to butenes and butadiene and butenes to butadiene has found particularly effective. Particularly preferred are acyclic paraffins and monoolefins having from 4 to 12 carbon atoms. Examples of suitable feedstocks include ethane, propane, n-butane, isobutane, pentane, hexane, 2-methylhexane, octane, 2,4-dimethyloctane, 2-methyl 1-butene, 2-hexene, 1-octene, 3-methyl-4-nonene, 1-dodecene and the like, the mixtures thereof.

The catalysts of the present invention consist essentially of nickel, lead, phosphorus, and optionally, an alkali metal, and combined oxygen. The catalysts of the present invention can contain each of the above-mentioned elements in amounts shown in the following table:

| Element | Weight Percent | |
|---|---|---|
| | Broad | Preferred |
| Nickel | 30–75 | 55–65 |
| Lead | 5–50 | 15–25 |
| Phosphorus | 0.1–7 | 0.5–3 |
| Alkali Metal* | 0–5 | 0.5–2 |

*When the alkali metal is potassium, the weight percent is as shown; when the alkali metal is other than potassium (lithium, sodium, rubidium or cesium) then such alkali metal is included in an amount which is equivalent, on an atomic basis, to the amounts shown above.

The percentages shown above are based upon a total weight of the finished catalyst, and the difference between the total weights of the above-named elements and 100 percent is made up by its oxygen content in amounts sufficient to satisfy the valences of each of the elements in the catalyst.

In a presently preferred embodiment the alkali metal component of the catalyst is potassium.

These catalysts can be supported on or diluted with conventional support materials such as silica, alumina, boria, magnesia, titania, zirconia and combinations thereof, as well as with other similar conventional materials known in the art.

In a presently preferred embodiment the catalytic compositions of the present invention are employed without a support material.

The catalysts of the present invention can be prepared by any suitable method including coprecipitation, impregnation and dry mixing, which provides the solid compositions previously described and which will have a surface area of at least about 1 m²/g. Substantially any nickel, lead, phosphorus and alkali metal compound can be used in the preparation of the catalytic material provided that none of the compounds are detrimental to the final catalysts, and so long as elements other than oxygen in the compounds used are substantially removed from the final catalytic composition by washing or by volitalization. In some instances, small amounts of other elements which may be present due to the starting compounds, can be tolerated in a final catalyst composition. For example, if a sulfate such as nickel sulfate is employed in the preparation, small residual amounts of sulfur can be tolerated. In general, the preferred nickel, lead, phosphorus and alkali metal compounds are either the oxides of these elements or compounds convertible to the oxides on calcination. Some examples of these are nickel nitrate, lead nitrate, lead monoxide, phosphoric acid, ammonium phosphate, potassium hydroxide and the like and mixtures thereof.

In one method of catalyst preparation, for example, suitable amounts of nickel and lead compounds are coprecipitated by mixing solutions of these compounds. The coprecipitation can be facilitated by the addition of a solution of an alkali metal or alkaline earth metal hydroxide to maintain the pH of the mixture from about 7 to about 10. The precipitate is filtered, washed to remove extraneous ions and then before or after drying, the precipitate is impregnated with a suitable phosphorus compound such as orthophosphoric acid. The composite is then dried.

Regardless of the specific sequence of steps utilized in the catalyst preparation method, the last stage of the preparation is activation by calcination in a molecular oxygen-containing gas such as air at a temperature of 750°–1800° F. (399°–982° C.) for 1 to 24 hours, or until the catalyst is active for oxidative dehydrogenation. The solid catalyst composition can be conventionally formed and utilized in any conventional shape or formed such as tablets, extrudates, granules, powder, and the like. Conventional lubricants such as polyethylene can be employed, if desired, in preparing the shaped catalytic material.

The dehydrogenatable feedstocks are converted according to the processes of the present invention at temperatures in the range of about 600°–1300° F. (315°–704° C.), preferably about 750°–1200° F. (399°–649° C.), at any convenient pressure such as from about 7 to 250 psia (48–1723 kPa), and at a volumetric hydrocarbon to oxygen ratio of from about 1:1 to about 1:4. The presence of steam is frequently beneficial and a volumetric steam to hydrocarbon ratio of up to 50:1 can be used. The hydrocarbon feed rate will generally be within the range of from about 50 to about 5000 GHSV (gas hourly space velocity, volume of hydrocarbon per volume of catalyst per hour). The fixed catalyst bed is the preferred mode of contact, but other modes such as a fluidized bed can also be used.

The dehydrogenation process is ordinarily carried out by forming a mixture, preferably a preheated mixture, of the dehydrogenatable feed, the oxygen-containing gas, and the steam, if used, and passing the mixture over the catalyst at the desired temperature. The effluent from the reaction zone is subjected to any suitable separation method to isolate and recover the desired product. Unconverted feeds or partially converted materials can be recycled to the dehydrogenation zone.

The dehydrogenation process is generally carried out in the absence of halogen in the feedstream, since the halogens are generally corrosive to the structural materials of the reactor and associated plumbing.

The catalyst of the present invention can be utilized for long periods of time without regeneration. However, when regeneration becomes necessary, this can be simply accomplished by merely cutting off the flow of dehydrogenatable feedstock and allowing the catalyst to be contacted with the oxygen and steam for a sufficient period of time to restore substantial activity to the catalyst.

Generally, at least trace amounts of oxygenated products are also formed in these reactions. For example, compounds such as furan, acetaldehyde, furfural and acetic acid and the like can be obtained. Some carbon oxides will be formed as well as some cracked products.

The following examples illustrate the invention.

EXAMPLE I

A series of three catalysts was prepared in which the catalyst composition was substantially identical except for the level of phosphorus. 4,500 g. of $Ni(NO_3)_2 \cdot 6H_2O$ and 500 g. of $Pb(NO_3)_2$ were dissolved together in distilled water to give 9 liters of solution. 2,100 g. of 85 percent KOH was separately dissolved in distilled water to give 5 liters of solution. The two solutions were added simultaneously and dropwise to 3 liters of water at a pH of 7–9. The resulting precipitate was filtered and washed with water to reduce the potassium content to about 1.5 weight percent.

A portion of the wet gel was impregnated with sufficient 85 percent $H_3PO_4$, diluted with water, to obtain a composite calculated on a dry basis to contain about 1 weight percent phosphorus. The impregnated gel was dried at 110° C. in a forced draft oven, ground and screened to pass a 40 mesh screen. A portion of the screened product was admixed with 6 weight percent solid polyethylene as the lubricant and formed into ¼"×⅛" (0.6×0.3 mm) tablets. The tablets were calcined for two hours at 900° F. (482° C.) and then for 2 hours at 1100° F. (593° C.). The product was ground and screened to obtain 20–40 mesh particles. This material is hereinafter referred to as Catalyst A.

A second portion of the wet gel was impregnated with sufficient 85 percent $H_3PO_4$, diluted with water, to obtain a composite calculated on a dry basis to contain about 1.5 weight percent phosphorus. This material, hereinafter referred to as Catalyst B, was dried, formed into pellets, calcined, ground and screened in the same manner as Catalyst A.

A third portion of the wet gel was impregnated with sufficient 85 percent $H_3PO_4$, diluted with water, to obtain a composite calculated on a dry basis to contain about 4 weight percent phosphorus. This catalyst, hereinafter referred to as Catalyst C, was dried, formed into pellets, calcined, ground and screened in the same manner as Catalyst A.

These catalysts had the compositions shown in Table I:

Table I

| Catalyst | Catalyst Compositions Weight Percent | | | |
|---|---|---|---|---|
| | Ni | Pb | P | K |
| A | 57.3* | 19.3* | 1.0* | 1.5* |
| B | 56.0 | 18.8 | 1.8* | 1.4 |
| C | 52.0 | 18.8 | 3.5* | 1.3 |

*Analyzed values. All other values are calculated.

EXAMPLE II

The effect of the phosphorus level on the activity of the nickel/lead/phosphorus/potassium catalyst of this invention was investigated. Catalysts A, B and C were used to promote the oxidative dehydrogenation of n-butane. In all runs, a temperature of 900° F. (482° C.), a volumetric feed:oxygen ratio of 1:1, a feed rate of 1000 GHSV, and a volumetric steam:feed ratio of 10 were employed. The data presented in Table II, below, were obtained after two hours on stream. The results are shown in the following table:

Table II

Effect of Phosphorus Level on Activity of Ni/Pb/P/K/O Catalysts

| Run | Catalyst | Wt. % P | Conversion | Selectivity[1] | Butadiene | Butenes | Cracked Products | Carbon Oxides |
|---|---|---|---|---|---|---|---|---|
| 1 | A | 1.0 | 23 | 37 | 0.0 | 8.5 | 1.6 | 12.6 |
| 2 | B | 1.8 | 37 | 71 | 10.2 | 15.9 | 0.0 | 10.7 |
| 3 | C | 3.5 | 7 | 88 | 0.0 | 5.9 | 0.0 | 0.8 |

[1]Gas phase selectivity to butadiene and butenes based on analysis of the gas phase products for converted hydrocarbons, carbon oxides and unconverted feed. The conversion and yield are reported on the same basis as the gas phase selectivity.

The above data indicate that the activity of the Ni/Pb/P/K/O catalysts in which the mole ratio of Ni:Pb is about 10:1 is influenced by the phosphorus level in the catalyst. Good conversion and gas phase selectivity to butadiene plus butenes was achieved when the catalyst contained 1.8 weight percent phosphorus, as shown in Run 2. Run 1 shows that when 1.0 weight percent phosphorus is present in the catalyst, the conversion declines to 23 percent and the gas phase selectivity to butenes declines to 37 percent. No butadiene was found in the reaction mixture of this run. Run 3 shows that when 3.5 weight percent phosphorus is present in the catalyst, the conversion declines to 7 percent, although gas phase selectivity to butenes remains good. However, as in Run 1, no butadiene was found in the product.

EXAMPLE III

The effect of dehydrogenation temperature in the dehydrogenation of n-butane was investigated using Catalyst B. With the exception of temperature, process conditions and feed rates were the same as shown in the Example II. Results are shown in the following table:

Table III

Effect of Temperature on Oxidative Dehydrogenation of n-Butane

| Run | Temp. °F. | Temp. °F. | Hours When Sampled | Conv., % | Sel., %[1] | Butadiene | Butenes | Cracked | Carbon Oxides |
|---|---|---|---|---|---|---|---|---|---|
| 4 | 700 | 371 | 150 | 9 | 92 | 2.4 | 5.8 | 0 | 0.7 |
| 5 | 750 | 399 | 122 | 16 | 89 | 2.7 | 11.3 | 0 | 1.7 |
| 6 | 800 | 427 | 102 | 23 | 83 | 6.3 | 13.1 | 0 | 4.0 |
| 7 | 850 | 454 | 72 | 35 | 74 | 10.7 | 15.3 | 0 | 9.3 |
| 8 | 900 | 482 | 62 | 36 | 74 | 10.5 | 15.9 | 0 | 9.4 |
| 9 | 900 | 482 | 192 | 39 | 73 | 11.3 | 16.9 | 0 | 10.4 |

[1]Same basis used as in Example II.

EXAMPLE IV

Catalyst B was used to promote the oxidative dehydrogenation of isopentane at 900° F. (482° C.) under the process conditions and feed rates used in Example II. The data shown in Table IV, below, were obtained after 60 hours on stream. The results are shown in the following table:

Table IV

Oxidative Dehydrogenation of Isopentane

| Run | Conv., % | Sel., % | Isoprene | Isoamylenes | Cracked | Carbon Oxides |
|---|---|---|---|---|---|---|
| 10 | 29 | 52 | 4.6 | 10.6 | 0.8 | 13.1 |

The data in the above table illustrates the operability of the catalyst of the present invention when applied to the oxidative dehydrogenation of isopentane.

While certain embodiments of the invention have been described for illustrative purposes, the invention is not limited thereto. Various other modifications or embodiments of the invention will be apparent to those skilled in the art in view of this disclosure. Such modifications or embodiments are within the spirit and scope of this disclosure.

We claim:

1. A process for the dehydrogenation of an acyclic paraffin or monoolefin feedstock having from 4 to 12 carbon atoms per molecule which comprises contacting a mixture of said feedstock and molecular oxygen with a catalyst containing about 56.0 weight percent nickel, about 18.8 weight percent lead, about 1.8 weight percent phosphorus and about 1.4 weight percent potassium, with the remainder being combined oxygen, at a temperature of about 900° F. a pressure in the approximate range of 7-250 psia and a volumetric hydrocarbon:oxygen ratio in the approximate range of 1:1 to 1:4.

2. The process of claim 1 wherein said feedstock is n-butane.

3. The process of claim 1 wherein said feedstock is isopentane.

* * * * *